US012746021B2

(12) United States Patent
Bartholomai et al.

(10) Patent No.: US 12,746,021 B2
(45) Date of Patent: Sep. 29, 2026

(54) EXTRACTOR CANNULA SECUREMENT AND PROCESSING

(71) Applicant: Cook Medical Technologies LLC, Bloomington, IN (US)

(72) Inventors: James Andrew Bartholomai, Louisville, KY (US); Shannon Jones, Greenwood, IN (US); Johnny P. Smith, Worthington, IN (US); Lyle Hundley, Bloomington, IN (US); Kristen M. Bunch, Bloomington, IN (US); Carmen Rosporski, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 361 days.

(21) Appl. No.: 18/450,204

(22) Filed: Aug. 15, 2023

(65) Prior Publication Data

US 2023/0404608 A1 Dec. 21, 2023

Related U.S. Application Data

(62) Division of application No. 17/144,459, filed on Jan. 8, 2021, now abandoned.

(Continued)

(51) Int. Cl.
*A61B 17/22* (2006.01)
*A61B 17/221* (2006.01)

(52) U.S. Cl.
CPC .... *A61B 17/221* (2013.01); *A61B 2017/2212* (2013.01)

(58) Field of Classification Search
CPC ........................ A61B 17/221; A61B 2017/221
See application file for complete search history.

(56) References Cited

U.S. PATENT DOCUMENTS

| | | | | |
|---|---|---|---|---|
| 5,064,428 A * | 11/1991 | Cope | .................... | A61B 17/221 606/127 |
| 6,302,895 B1 * | 10/2001 | Gobron | ................ | A61B 17/221 606/127 |

(Continued)

FOREIGN PATENT DOCUMENTS

| | | | | |
|---|---|---|---|---|
| DE | 102012222356 A1 * | 6/2014 | ........... | A61B 17/221 |
| GB | 2448123 A * | 10/2008 | .............. | B21F 45/16 |

(Continued)

OTHER PUBLICATIONS

Extended European search report dated Jun. 1, 2021 (5 pages) from EP Application No. 21 151 225.6.

(Continued)

*Primary Examiner* — Bayan Salone
(74) *Attorney, Agent, or Firm* — Crowell & Moring LLP

(57) ABSTRACT

A medical retrieval device for retrieving stones, calculi, and the like from various organs and passages may comprising an elongated member, and a first wire and a second wire that forms a retrieval basket. The wires forming the basket and the elongated member may be secured by a crimp joint and a second joint. Processing of the device may include placing all ends of the first wire and the second wire into an elongated member through a distal end of the elongated member, moving said elongated member to a position where the first loop and the second loop start their curvatures, placing said first and second wires and said elongated member through a crimping fixture having thru cuts configured for the interlocked wires, aligning said elongated member in a desired position, and crimping said first and second wires and said elongated member.

12 Claims, 6 Drawing Sheets

Related U.S. Application Data

(60) Provisional application No. 62/960,348, filed on Jan. 13, 2020.

(56) References Cited

U.S. PATENT DOCUMENTS

| | | | | |
|---|---|---|---|---|
| 7,731,722 | B2 * | 6/2010 | Lavelle | A61B 17/221 606/127 |
| 8,043,303 | B2 * | 10/2011 | Razvi | A61B 17/2909 606/127 |
| 8,206,401 | B2 * | 6/2012 | Nakao | A61B 17/32056 606/127 |
| 9,101,342 | B2 * | 8/2015 | Saleh | A61B 10/02 |
| 9,149,289 | B2 * | 10/2015 | Teague | A61B 17/221 |
| 9,480,491 | B1 * | 11/2016 | Dostal | A61B 17/22031 |
| 9,642,637 | B1 * | 5/2017 | Lind | A61B 17/221 |
| 10,029,281 | B2 * | 7/2018 | Knepp | B21F 27/02 |
| 12,357,331 | B2 * | 7/2025 | Kenwood | A61B 17/320708 |
| 2004/0133213 | A1 * | 7/2004 | Bagley | A61B 17/221 606/127 |
| 2009/0030427 | A1 | 1/2009 | Razvi et al. | |
| 2013/0023893 | A1 * | 1/2013 | Saleh | A61B 10/04 606/113 |
| 2016/0166269 | A1 * | 6/2016 | Teague | B23K 26/38 219/121.85 |
| 2019/0223995 | A1 * | 7/2019 | Besselink | A61F 2/0108 |
| 2019/0240022 | A1 * | 8/2019 | Rafiee | A61F 2/2451 |

FOREIGN PATENT DOCUMENTS

| | | | | |
|---|---|---|---|---|
| GB | 2448123 B | | 5/2010 | |
| WO | WO-2009121379 A1 | * | 10/2009 | A61B 17/22031 |

OTHER PUBLICATIONS

Examination Report for corresponding EP Application No. 21151225.6 mailed Mar. 29, 2023, 5 pages.

* cited by examiner

EXTRACTOR CANNULA SECUREMENT AND PROCESSING

CROSS-REFERENCE TO RELATED APPLICATIONS

This application is a divisional of application Ser. No. 17/144,459, filed Jan. 8, 2021, which claims the benefit of the filing date under 35 U.S.C. § 119(e) of Provisional U.S. Patent Application Ser. No. 62/960,348, filed Jan. 13, 2020. All of the foregoing applications are hereby incorporated by reference in their entirety.

BACKGROUND

Various organs and passages in the body are subject to the development of stones, calculi, and the like. For example, gallstones are a common problem in the United States and the most frequent cause of gallbladder inflammation. Calculi in other parts of the biliary system and/or the urinary system are also common places. Medical retrieval devices for capturing and extracting stones from various organs and passages are well known. Such devices typically comprise a retrieval basket attached to a distal end of an elongated member.

Urological baskets, and other baskets, often utilize a glue joint to secure the basket formation into the desired orientation. It is desired to use other methods to construct a stone management basket such as for the benefits of limiting the cost, both in labor and in material, to manufacture a stone management basket as well as for repeatability and other quality control factors.

BRIEF SUMMARY

Embodiments of the present disclosure relate to, among other things, securement and processing of medical retrieval devices. Each of the embodiments disclosed herein may include one or more of the features described in connection with any of the other disclosed embodiments.

One general aspect of the present disclosure includes a medical retrieval device for retrieving stones, calculi, and the like, as well as polyps, foreign objects, and/or anatomical abnormalities from various organs and passages, comprising an elongated member, and a first wire and a second wire that forms a retrieval basket. The elongated member has a hollow passageway longitudinally positioned therebetween, and the first wire having first and second ends attached to the distal end of the elongated member and forming a first loop extending longitudinally and distally from said distal end of the elongated member. The second wire likewise has its first and second ends attached to the distal end of the elongated member, forming a second loop extending longitudinally and distally from the distal end of the elongated member. The second loop is interconnected distally to said first loop, which interconnection may include one or more of conjoined loops, cannula, weld, solder, or other connection means known in the art for the distal end of wire baskets. The elongated member and the first and second wires are secured by a crimp joint and a second joint, where such joints can be secured by a cannula, welding, and/or soldering in addition to and/or instead of crimping.

Another general aspect of the present disclosure includes processing of the device disclosed above, processing comprising steps of placing all ends of the first wire and the second wire into an elongated member through a distal end of the elongated member, moving said elongated member to a position where the first loop and the second loop start their curvatures, placing said first and second wires and said elongated member through an alignment fixture such as a crimping or other securement fixture having thru cuts configured for the interlocked wires, aligning said elongated member in a desired position, and crimping said first and second wires and said elongated member, where such joints can be secured by a cannula, welding (including laser welding), glue, and/or soldering in addition to and/or instead of crimping.

Other systems, methods, features and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTION OF THE DRAWINGS

The present disclosure can be better understood with reference to the following drawings and description. The components in the figures are not necessarily to scale, emphasis instead being placed upon illustrating the principles of the present disclosure. Moreover, in the figures, like-referenced numerals designate corresponding parts throughout the different views.

DETAILED DESCRIPTION

Figure 1:
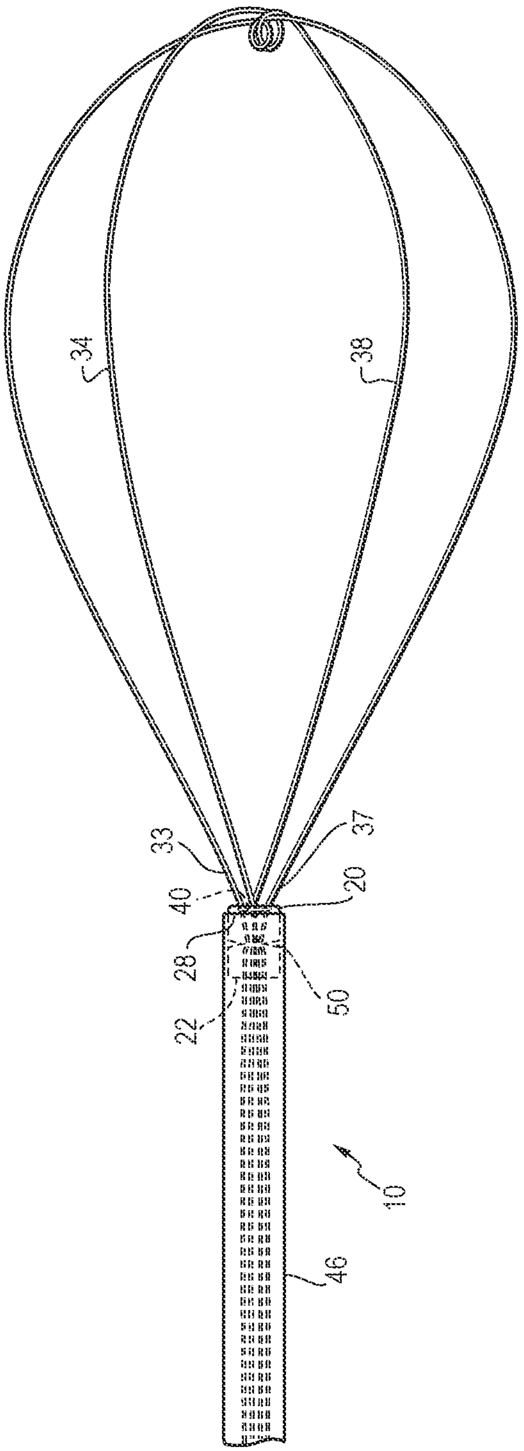
FIG. 1 is an illustration showing a distal portion of a retrieval device in accordance with certain non-limiting aspects of the present disclosure, where alternative basket and/or snare configurations may be used with the retrieval device.

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional material, construction, and assembly.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body.

Figure 2:
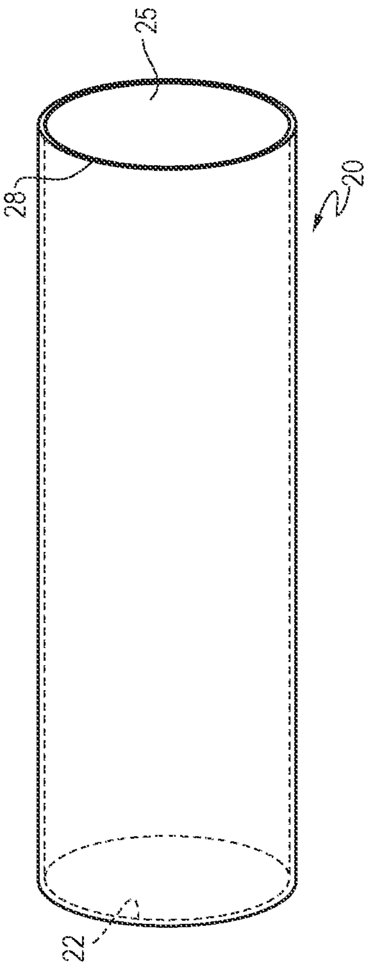
FIG. 2 is an illustration showing an elongated member in accordance with certain aspects of the present disclosure.
Figure 3:
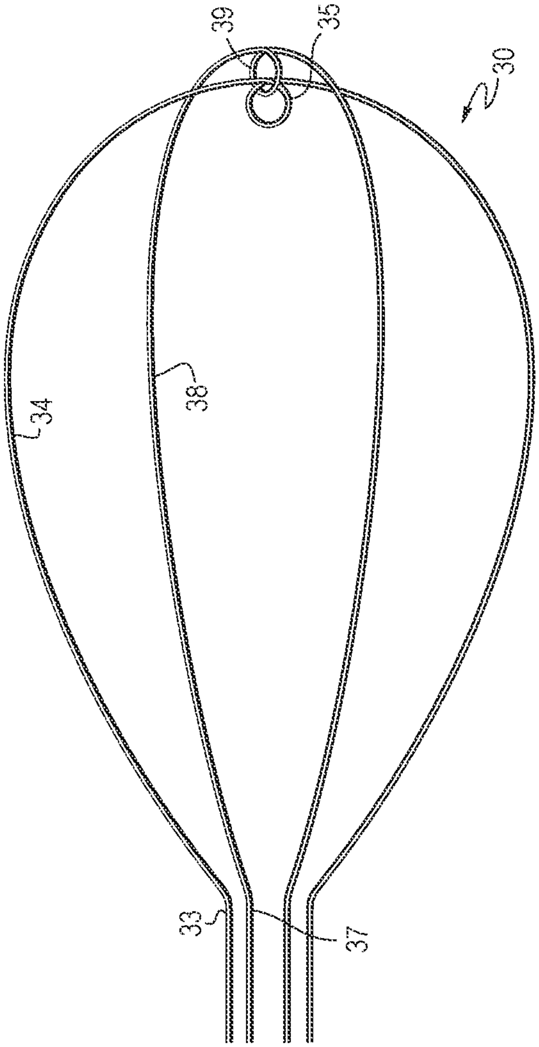
FIG. 3 is an illustration showing a retrieval basket in accordance with certain aspects of the present disclosure.

Referring to FIG. 1, a retrieval device 10 may comprise an elongated member 20 (such as, for example, a cannula), a retrieval basket 30, a crimp joint 50 and an additional/second joint 40. As illustrated by FIG. 2, the elongated member 20 may generally comprise a proximal end 22, a distal end 28, and a hollow passageway 25 longitudinally positioned therebetween. The elongated member 20 may be made of a metal such as stainless steel. Other flexible or rigid materials may also be utilized. The retrieval basket 30 may comprise a plurality of wires 34, 38 attached to the distal end 28 of the elongated member 20. The basket may include multiple loops of wires that interact with each other in order to be used in a stone management clinical setting, or for other retrieval uses when deployed a patient. The term "loop" should be understood to encompass a variety of shapes and not merely a circular or elliptical configuration, but also—by way of non-limiting example, helical, diamond-shaped, and/or other wire-shapes capable of defining a central volume to capture and/or carry a stone or other material. The basket can be preformed into any desired shape or size for capturing and removing calculi from the biliary or urinary system. Dimensions should be on scale with the size of the retrieval device. For example, the diameter of the device 10 may range from 1.5Fr to 4.5 Fr. The wires 34, 38 may be made from a nickel titanium alloy such as nitinol. As illustrated by FIG. 3, in one embodiment, the basket 30 may comprise two wires 34, 38, each forming loops extending longitudinally and distally from the distal end of the elongated member 28. In some embodiments, the wires 34, 38 may be interconnected perpendicularly relative to each other at the distal end and/or along planes defined by the respective loop formed by each wire 34, 38. In one embodiment, the large loop of wire 38 includes a distal-end small loop 39 that interconnects/links in a chain-like manner with a distal-end small loop 35 of the wire 34. Alternative embodiments may include different wire geometries (e.g. pie wire, round, square, D-shaped, etc.), wire quantities, and/or cannula geometries.

In one embodiment, the second joint 40 may be an adhesive such as glue. The adhesive may temporarily or permanently secure the wires 34, 38. Ideally, low viscosity cyanoacrylate glue, such as Loctite 4061, may be used for its strong adhesion to metal, wicking properties, and fast cure time. Alternative embodiments may include different glue compositions, and glue properties and application parameters should be selected to ensure appropriate adhesive dispersion. When using an adhesive, such as glue, as the second joint, a notchless cannula design may be advantageous to provide additional surface area for gluing and crimping.

In another embodiment, the second joint 40 may be a heat shrink. Ideally, a heat shrink, which may be activated using a heat gun, would have a melting temperature lower than the temperature at which the wires 34, 38 are formed (roughly 400° C.) so that the wires 34, 38 are not adversely affected during the heat shrink process. Exemplary heat shrink materials may include PTFE and PEBAX. One advantage of this embodiment is that the wires 34, 38 are kept in a desired formation throughout the functioning life of the retrieval device 10. Another advantage of this embodiment is that it may replace the need to use a metal cannula and give the retrieval device 10 a higher degree of flexibility when used inside a scope for a procedure.

In one embodiment, processing of the retrieval device may generally include placing all four ends of the wires 34, 38 into the elongated member 20 through its hollow passageway 25, moving the elongated member 20 to the bottom of the wires 33, 37 where the wires 34, 38 end their curvature and go straight. Then, the wires 34, 38 and the elongated member 20 may be placed through an alignment fixture or other securement fixture such as crimping fixture 100 having thru cuts configured for the interlocked wires 34, 38 to ensure that the wires 34, 38 are aligned properly. Once the wires 34, 38 and the elongated member 20 are properly aligned, they may be crimped to form a crimp joint 50. A second joint 40 may be formed prior to forming the crimp joint 50.

Figure 4A:
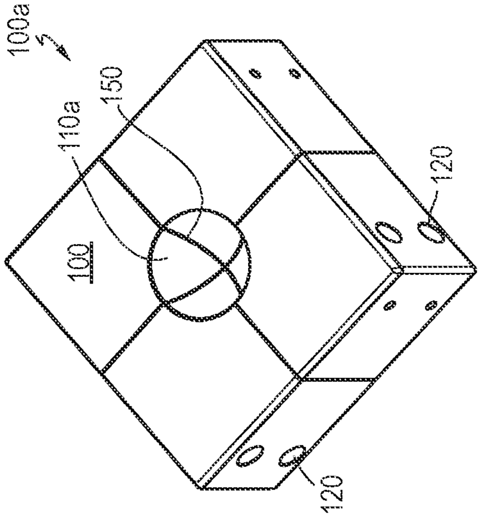
FIGS. 4A-4D are illustrations showing various non-limiting crimp or other alignment fixture designs for processing of the device, where other securement means such as a cannula, welding (including laser welding), glue, and/or soldering in addition to and/or instead of crimping may be used.
Figure 4B:
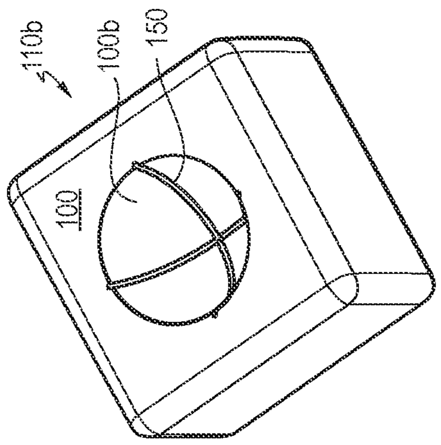
Figure 4C:
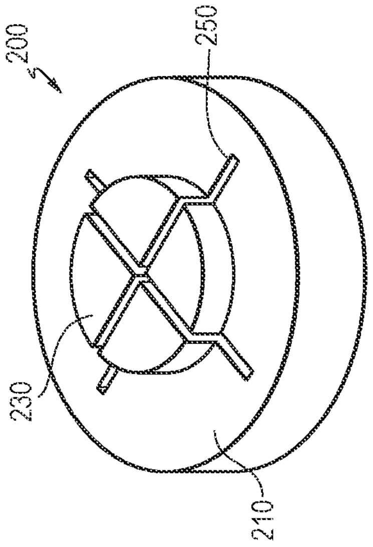
Figure 4D:
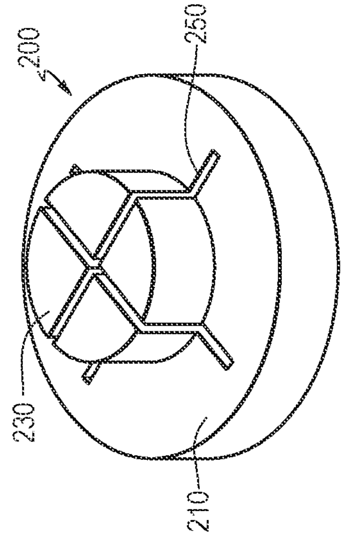
Figure 5:
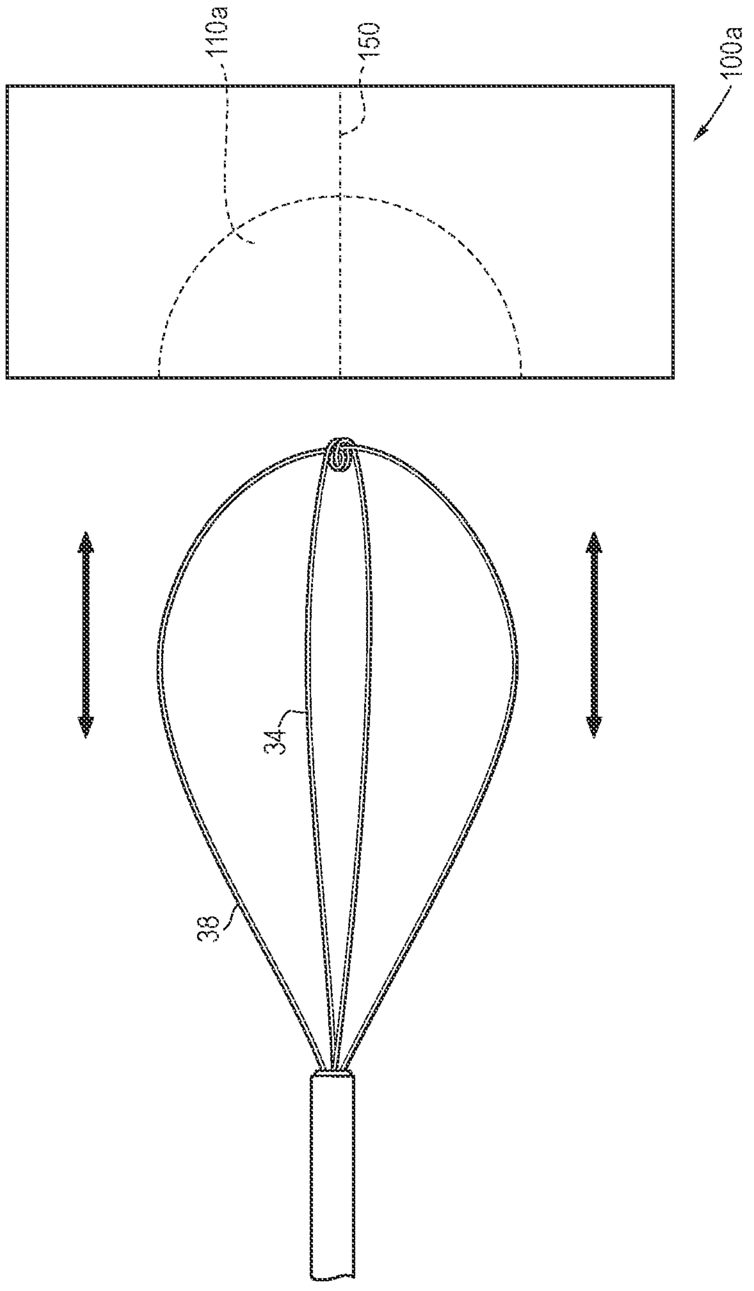
FIG. 5 is an illustration showing how wires of the device may interact with, for example, a crimping fixture in accordance with certain aspects of the present disclosure.

In one embodiment, formation of a crimp joint 50 may utilize a crimping fixture or other alignment fixture 100 to ensure that the wires 34, 38 hold their desired relationship during the crimping process. Specifically, crimping fixture or other alignment fixture 100*a*, 100*b*, 200 has a cross-hair thru cut 150, 250 all the way through the part to allow a distal or proximal end of the basket 30 to be fed through it before and/or after crimping. Alternatively, crimping fixture 100*a*, 100*b*, 200 may have a blind cut (not shown in figures) instead of thru cut 150, 200. Referring to FIGS. 4A-4D, crimping fixture 100*a*, 100*b*, 200 may have a thru cut 150, 250 that slides in the wires 34, 38 interconnected perpendicularly. Specifically, configurations illustrated in FIGS. 4A-4B have an indented area 110*a*, 110*b* in the middle to help the basket wires 34, 38 slide into the fixture. FIG. 5 illustrates how wires 34, 38 may interact with crimping fixture 100*a*. Indented area 110*a* may help wires 34, 38 to slide all the way into the fixture 100*a* through the thru cut 150. Other crimping fixtures as illustrated by FIG. 4B-4B may interact with wires 34, 38 in a similar manner. More specifically, the fixture of FIG. 4A has openings 120 on the side to allow assembly with screws (screws not shown in figures). The fixture of FIG. 4B, the fixture does not have openings 120 on the side for screw assembly, but instead has smaller area outside of the indented area 110*b*. The thru cut 150 should have a tight tolerance to keep the wires 34, 38 in line. For example, the length and width of thru cuts 150 may be 0.590 inches and 0.020 inches, respectively. As illustrated by FIGS. 4C and 4D, in another embodiment, crimping fixture 200 may comprise a base section 210 and an elongated section 230 to help get the fixture 200 closer to the crimping site. Specifically, the diameter of the base section 210 may be greater than the diameter of the elongated section 230. For example, the diameter of the base section 210 may be 0.750 inches while the diameter of the elongated section 250 may be 0.375 inches. Further, the thickness of base section 210 may be 0.157 inches. The thickness of the elongated section 250 may range from 0.079 inches to 0.154 inches. The crimping fixture 200 may also have the thru cut 250. As with alternative embodiment described above, the thru cut 250 should have a tight tolerance to keep the wires 34, 38 in line. Specific dimensions should be on scale with the size of the retrieval device 10, thus may vary.

Figure 6:
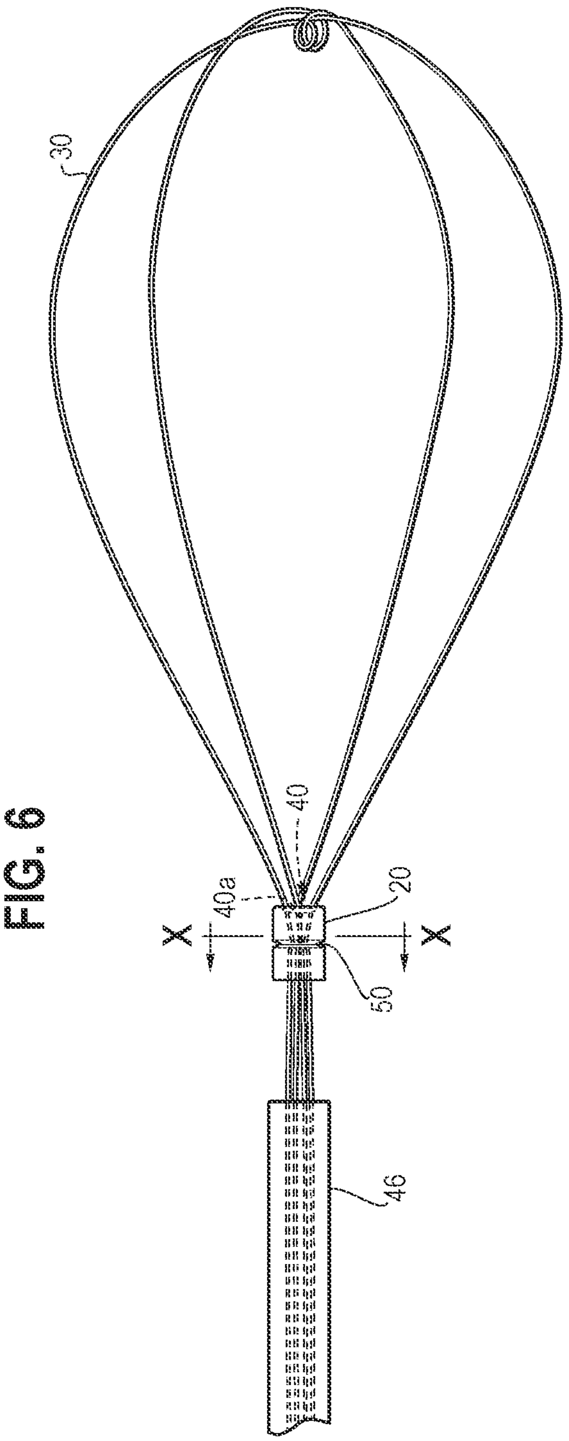
FIG. 6 is an illustration showing assembly of the device in accordance with certain aspects of the present disclosure.
Figure 7A:
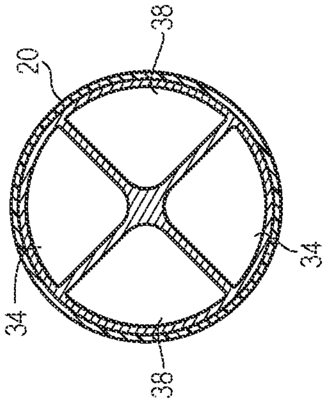
FIGS. 7A-7F are illustrations showing various cross sectional configurations, taken along line X-X of FIG. 6, near a crimp joint as described within the scope of the present disclosure.
Figure 7B:
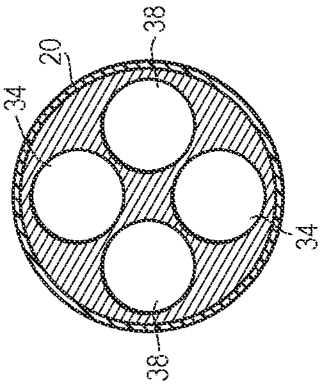
Figure 7C:
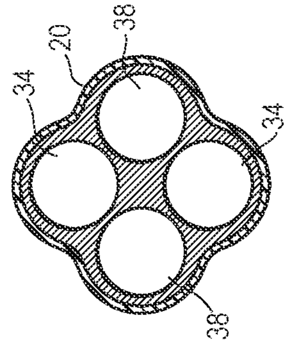
Figure 7D:
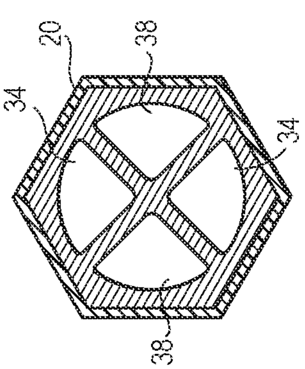
Figure 7E:
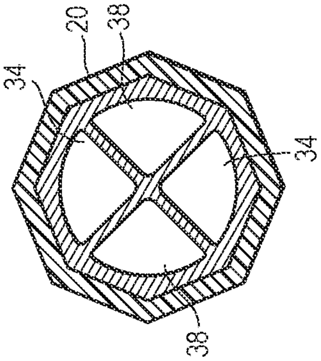
Figure 7F:
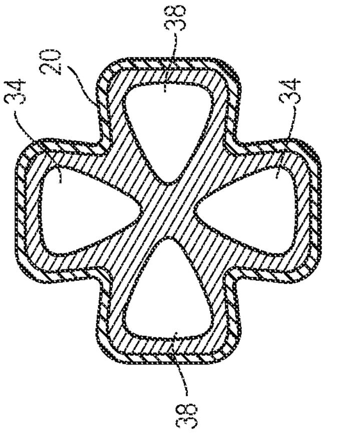

Referring to FIG. 6, processing of a device with a glue 40*a* or other secondary securement means (such as, by way of non-limiting example, weld or solder) 40*a* as part of a second joint 40 may include steps of aligning the wires 34, 38 inside an elongated member 20 to ensure that the wires 34, 38 are shaped correctly to form a basket of a desired configuration. Aligning may include pulling the wires 34, 38 into an alignment sheath (not shown) to assure a proper alignment and then removing the alignment sheath while maintaining the alignment. After removing the alignment sheath, the glue may be applied to the distal end 28 of the elongated member 20 or elsewhere within the elongated member 20. Once the glue 40*a* cures, a sheath 46 may be pulled over the elongated member 20 before or after the act of crimping. As shown in the drawings, the proximal half of the elongated member 20, where no glue 40*a* presents, may be crimped with the wires 34, 38. But, this crimp 50 and/or additional crimp joints 50 may be placed as needed or desired, proximal and/or distal of the glue or other secondary securement means in embodiments were such secondary securement means are present.

Processing an embodiment using a heat shrink as an elongated body 20 may comprise steps of placing all ends of the wires 34, 38 in a heat shrink, moving the heat shrink (20) to the wires' bottom portions 33, 37 where the wires 34, 38 end their curvature and go straight or substantially straight as compared to the loop portions. Further, processing may include turning a heat gun to a desired temperature, placing all ends of the wires 34, 38 and the heat shrink at a desired distance from the heat gun for a designated time. Once the heat shrink and the wires 34, 38 cool down and an inspection confirms a proper alignment, which may be perpendicular, one may proceed to further process the device 10.

In another embodiment, a short crimper that can crimp down to 0.010" at a force greater than 100 lbs. may be used to form a crimp joint 50. It is important to ensure that the pressure setting for the crimping fixture is set to the correct final outside diameter and that the pressure is high enough. The area of crimp joint 50 after crimping with a short crimper may have a hexagonally shaped cross-section, or another geometric shape (e.g., octagonal, circular, elliptical, or other shape, depending upon the shape of the crimping mechanism/surface contacting the crimp joint 50 during formation thereof, with reference to non-limiting examples in FIGS. 7A-7F, where "geometric" is defined as "utilizing rectilinear or simple curvilinear motifs or outlines that bear little resemblance to natural/organic forms"). In some embodiments, as illustrated by FIGS. 7A-7F, the region near and/or including the crimp joint 50 may have different cross-sectional configurations (as viewed along line X-X of FIG. 6) after the wires are aligned and secured together. Certain embodiments, such as FIGS. 7A, 7D, 7E, and 7F, may advantageously include a pie-shaped wire, also called "delta wire", because the added angles may help keep the wires 34, 38 in the perpendicular relationship.

Although some preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

We claim:

1. A method of making a medical device having a first wire, a second wire, and an elongated member, comprising steps of:

placing all ends of the first wire and the second wire into an elongated member so that the first wire forms a first loop and the second wire forms a second loop, where the first loop and the second loop each form a curvature out of a primary longitudinal axis of, respectively, the first wire and the second wire;

moving said elongated member to a position where the first loop and the second loop start their curvatures;

aligning said elongated member and said first and second wires in a desired position relative to each other, wherein the step of aligning said elongated member and said first and second wires in a desired position relative to each other includes placing said first and second wires and said elongated member through an alignment fixture; and crimping said first and second wires and said elongated member.

2. The method of claim 1, further comprising:

distally interlocking the second wire to the first loop prior to the step of placing all ends of the first wire and the second wire into an elongated member through a distal end of the elongated member.

3. The method of claim 2, further comprising configuring said first wire and said second wire being disposed perpendicularly relative to each other where the first wire and second wire are distally interlocked.

4. The method of claim 1, wherein the alignment fixture further includes a longitudinally elongated section that allows the fixture to get closer to a crimping site.

5. The method of claim 1, further comprising applying a second securement to the elongated member after placing all ends of the first wire and the second wire into said elongated member through a distal end of said elongated member.

6. The method of claim 1, further comprising:

placing all ends of the first wire and the second wire into a heat shrink;

moving the heat shrink to a position where the first loop and the second loop start their curvatures;

heating the heat shrink member and all ends of the wires for a designated time; and cooling the heat shrink member, the first wire, and the second wire prior to placing all ends of the first wire and the second wire into said elongated member through the distal end of said member.

7. The method of claim 1, wherein the crimping step includes using a crimper that crimps the elongated member in a manner forming a crimp joint that includes a geometric shape.

8. The method of claim 1, further comprising steps of:

forming a secondary loop of the first wire and a secondary loop of the second wire;

distally interlocking the secondary loop of the first wire in chain-like fashion with the secondary loop of the second wire, before the step of placing all ends of the first wire and the second wire into an elongated member.

9. The method of claim 8, where the interlocked secondary loops are disposed at a distalmost end of the first loop and the second loop, and where the first loop is perpendicular to the second loop.

10. The method of claim 4, where the step of aligning includes the alignment fixture holding the first wire and the second wire in a desired orientation.

11. The method of claim 10, where the alignment fixture includes one or more of a thru-cut, a blind cut, and screws disposed to secure the desired orientation.

12. A method of making a medical device having a first wire, a second wire, and an elongate member, comprising steps of:

placing all ends of the first wire and the second wire into an elongate member so that the first wire forms a first loop and the second wire forms a second loop;

moving the elongate member to a position where the first loop and the second loop start their curvatures;

placing the first and second wires and the elongate member through an alignment fixture having cuts configured for receiving the wires;

aligning said elongate member in a desired position;

where the elongate member is configured as a crimpable cannula or as a heat shrink member; and wherein, when the elongate member is configured as a crimpable cannula, a step of crimping said first and second wires and said elongate member, or when the elongate member is configured as a heat shrink member, a step of heating the heat shrink member and all ends of the wires for a designated time.

* * * * *